United States Patent [19]

Thorsen

[11] Patent Number: 5,361,639
[45] Date of Patent: Nov. 8, 1994

[54] TENSILE TESTING DEVICE

[76] Inventor: Helge Thorsen, Molybdenveien 8, N-4629 Kristiansand, Norway

[21] Appl. No.: 121,537

[22] Filed: Sep. 16, 1993

[30] Foreign Application Priority Data

Sep. 18, 1992 [NO] Norway ............... 923639

[51] Int. Cl.⁵ .................. G01N 3/08; G01N 19/04
[52] U.S. Cl. ................... 73/827; 73/150 A; 156/378
[58] Field of Search .......... 73/827, 150 A; 156/378

[56] References Cited

U.S. PATENT DOCUMENTS

| | | | |
|---|---|---|---|
| 3,527,093 | 9/1970 | Sellers | 73/150 A |
| 3,628,378 | 12/1971 | Regan, Jr. | 73/827 |
| 3,821,892 | 7/1974 | Säberg | 73/827 |
| 4,491,014 | 1/1985 | Seiler, Jr. | 73/150 A |
| 4,586,371 | 5/1986 | Ivie et al. | 73/827 |
| 4,893,513 | 1/1990 | Schroeder et al. | 73/150 A |

FOREIGN PATENT DOCUMENTS

| | | | |
|---|---|---|---|
| 1455534 | 11/1976 | United Kingdom | 73/150 A |
| 317959 | 1/1972 | U.S.S.R. | 73/150 A |
| 389420 | 12/1973 | U.S.S.R. | 73/827 |

*Primary Examiner*—Thomas P. Noland
*Assistant Examiner*—Daniel S. Larkin
*Attorney, Agent, or Firm*—Brody and Neimark

[57] ABSTRACT

A hydraulically driven, dynamic tensile testing device wherein a test sample attached to an underlying surface can be secured to the device and subjected to tensile forces in that the device is raised from the underlying surface, where the device rests against the underlying surface on three or more legs connected to interacting pistons (6). The interacting pistons are preferably hydraulic pistons that are pressurized by means of a hydraulic fluid which is distributed through interconnected ducts in such a way that the legs have a constant, even pressure. The device thus ensures that the tensile forces are evenly distributed on the cross-section of the test sample.

10 Claims, 1 Drawing Sheet

TENSILE TESTING DEVICE

BACKGROUND OF THE INVENTION

1. Technical Field

The present invention relates to a hydraulically driven, dynamic tensile testing device for carrying out tests such as measuring the adhesive properties of a coating on a substrate or tensile testing materials that possess little elasticity.

During tensile testing, it is of vital importance that the tensile forces are evenly distributed over the cross-section of the test sample. A slight unevenness can result in that only a part of the cross-section of the sample is subjected to the measured forces. This could result in excessively low measured values for the tensile strength of the test specimen and measurements that are barely reproducible. Elastic test samples can compensate for uneven tension to a certain extent, but in the case of thin test samples, such as when measuring the adhesion of a coating to a substrate and when tensile testing inelastic materials, the materials will not be able to even out any uneven loads.

Tensile measuring of materials possessing little elasticity is therefore performed with extremely expensive specialized equipment operated by highly qualified personnel who have been especially trained.

The adhesion of a coating, e.g., paint, to an underlying surface is, for many uses, of vital importance. An inadequate adhesion to the underlying surface can result in the loosening and peeling off of the coating, and thus the loss of the protection which the coating is supposed to provide the underlying surface. Therefore, a minimum requirement for such adhesion is often made, a requirement that must be capable of being checked with reproducible and reliable measurements. The problems are often the same for a coating as for materials of little elasticity. An uneven load cannot be compensated for by the elasticity of the coating as the coating is relatively thin.

2. Prior Art

A number of devices for measuring the adhesion of a coating to a substrate are known. All the devices are based on a test piston fixed by glue to the substrate being pulled vertically upwards therefrom. The force that is needed to cause the coating to come away from the substrate gives a measurement of the adhesion of the coating to the substrate. In order to provide reliable and reproducible measurements, it is important that the tractive force is vertical to the surface and is evenly distributed over the test surface. If the tractive force is not vertical to the substrate, this may result in the coating being ripped up from one side, thereby giving inaccurate and non-reproducible measurements of the adhesion.

GB 1 179 149 makes known a device which is equipped with a torque arm and is therefore supplied with torsional force which is difficult to avoid. This device is also equipped with legs that can be adjusted by means of nuts in order to arrive at vertical tractive force. However, it can be difficult or even impossible to adjust the legs with the accuracy required in order to obtain an even distribution of the forces on the test surface, namely a deviation of less than a few $\mu m$.

SE 379 243 makes known a device that is revolvably mounted on two legs. This device provides a relatively reliable measurement result, but it is large, heavy and dependent upon the use of a gas cylinder, and this makes the device rather unsuitable for use in the field.

OBJECT AND SUMMARY OF THE INVENTION

The objective of the present invention is thus to provide a tensile testing device, for carrying out tests such as measuring the adhesion of a coating to a substrate or the tensile testing of materials that are virtually inelastic, which provides reliable and reproducible results.

A second objective is to provide a testing device that is easy to use, that is of a simple structure, that minimizes operator errors, and that is as serviceable in the field as in the laboratory.

According to the invention, this is achieved by a hydraulically driven, dynamic tensile testing device where a test sample attached to an underlying surface can be secured to the device and subjected to tensile forces in that the device is raised from the underlying surface, characterized in that the device rests against the underlying surface on three or more legs connected to interacting pistons.

To ensure that the pistons have equal pressure and thus that the tractive forces are evenly distributed on the test surface, the hydraulic fluid, according to the invention, is distributed to all the hydraulic pistons through interconnected ducts.

The testing device according to the invention is made simple to operate in that a test piston or a test specimen can be attached to the testing device by means of a quick release coupling.

The invention will now be described in more detail and with reference to the attached figures.

DETAILED DESCRIPTION OF THE PREFERRED EMBODIMENTS

Figure 1:
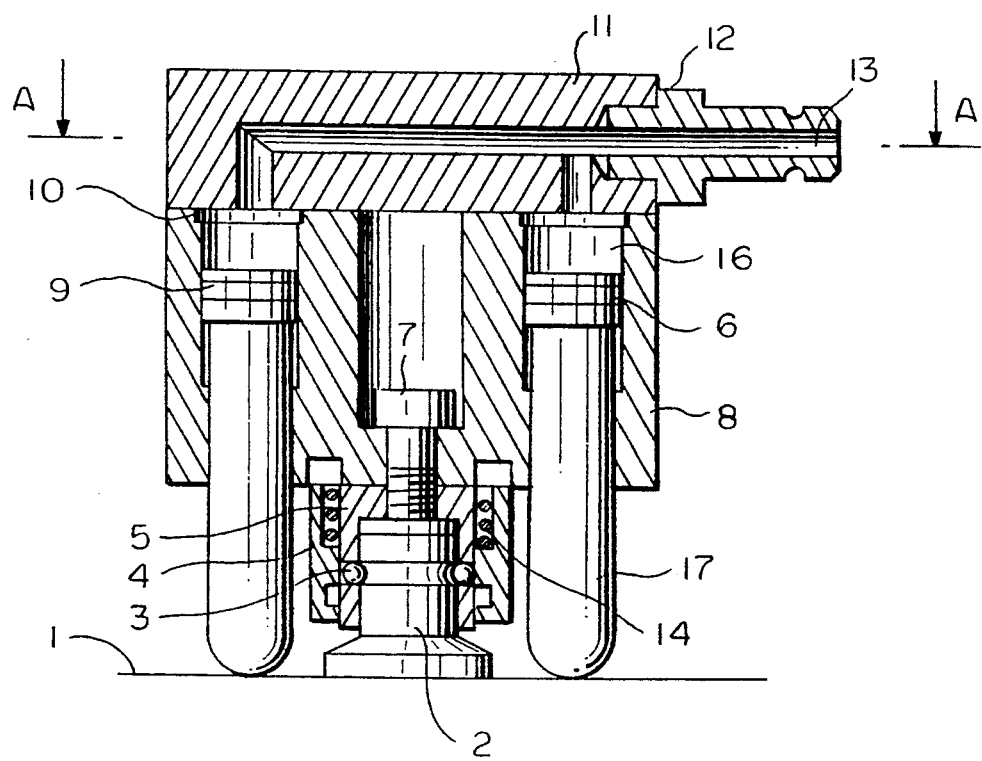
FIG. 1 is a cross-sectional elevational view through the tensile testing device according to the invention.

FIG. 1 is a cross-sectional view of a device for adhesion testing that is set up to test the adhesion of a coating (1) to a substrate. The coating can be of any kind whatsoever, eg, paint. The test piston (2) is glued to the coating (1) by means of an adhesive that is commonly used in this art. The test piston (2) is attached to the testing device by means of a quick release coupling which consists of balls (3), an outer ring (4) and an inner ring (5) and a spring (14) and is attached to the testing device by means of a screw (7).

Figure 2:
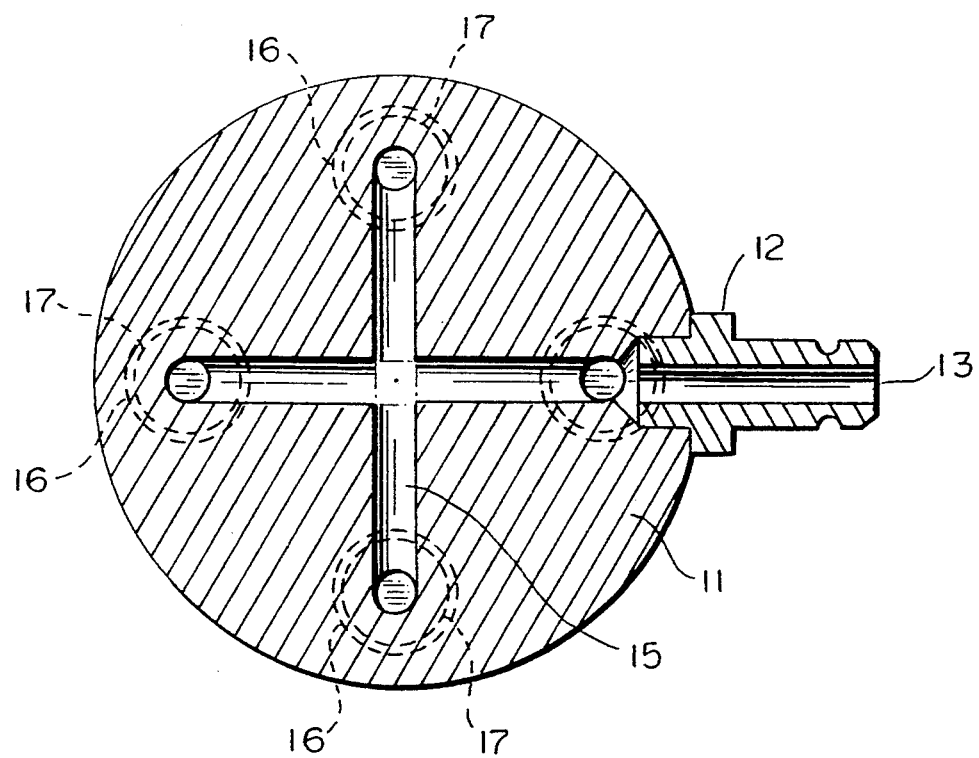
FIG. 2 is a cross-section through section A—A of FIG. 1.

Three or more hydraulic interacting pistons (6) engaged to legs (17) shown on FIGS. 1 and 2; reside in the cylinder housing (8) and are pressurized with hydraulic fluid (13) that is distributed via an interconnected duct system (15) to piston chambers (16) so that all the pistons have equal pressure. Unevenness in the underlying surface, such as unevenness in the coating or the substrate and curved surfaces will therefore be compensated for in such a way that the test piston (2) is pulled up from the coating with a force that is evenly distributed through legs (17) over the whole test surface.

The hydraulic fluid (13) is pumped into the testing device by means of a pump or other pressure transmitter via a quick release coupling (12). The pressure of the hydraulic fluid will thus be proportional to the force with which the test piston is raised.

The adhesion of the coating to the substrate can thus be calculated as a function of the pressure in the hydraulic fluid when the coating comes away from the substrate.

Packings (9, 10) provide a seal between the cylinder housing (8) and the piston (6) and between the cylinder housing (8) and the top (11), respectively.

The same device can also be used for tensile testing of materials that possess little elasticity such as hardened steel, ceramic materials and bone. The test piston (2) can be replaced by the test sample which is to be measured or can be replaced by a fixture for the sample. At the other end the sample is fixed to an underlying surface. The interacting pistons (6) will ensure an even distribution of the forces over the cross-section of the test sample, thereby providing reproducible and reliable measurements in the same way as when measuring adhesion.

The hydraulic fluid can also be replaced by a gas and the hydraulic pistons can be replaced by pneumatic pistons. The testing device can also be constructed with a different number of legs (17) if, for various reasons, this is so desired.

I claim:

1. A hydraulically driven, dynamic tensile testing device where a test sample attached to an underlying surface can be secured to the device and subjected to tensile forces in that the device is raised from the underlying surface, characterized in that the dynamic tensile testing device rests against said underlying surface on three or more legs (17) connected to interacting pistons (6).

2. A device according to claim 1, characterized in that a pressure fluid is distributed to all the enteracting pistons (6) through interconnected ducts (15).

3. A device according to claim 2, characterized in that the pressure fluid is a hydraulic fluid and the interacting pistons (6) are hydraulic pistons.

4. A device according to claim 3, characterized in that the test sample can be fixed to the dynamic tensile testing device via a test piston (2) which is secured to the testing device at one end and to the test sample at an other end.

5. A device according to claim 4, characterized in that the test sample or test piston (2) can be secured by means of a quick release coupling (3-5).

6. A device according to claim 2, characterized in that the pressure fluid is a gas and the interacting pistons (6) are pneumatic pistons.

7. A device according to claim 6, characterized in that the test sample can be fixed to the dynamic tensile testing device via a test piston (2) which is secured to the testing device at one end and to the test sample at an other end.

8. A device according to claim 7, characterized in that the test sample or test piston (2) can be secured by means of a quick release coupling (3-5).

9. A method of using a device according to claim 1 for measuring adhesion of a coating to a substrate.

10. A method of using a device according to claim 4 for measuring adhesion of a coating to a substrate.

* * * * *